US011653903B2

(12) United States Patent
Wang et al.

(10) Patent No.: US 11,653,903 B2
(45) Date of Patent: May 23, 2023

(54) AUTOMATIC REFLECTION HAMMER SYSTEM

(71) Applicant: Chang Gung University, Taoyuan (TW)

(72) Inventors: Jer-Chyi Wang, Taoyuan (TW); Yi Fu, Taoyuan (TW); Kuo-Hsuan Chang, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 925 days.

(21) Appl. No.: 16/565,537

(22) Filed: Sep. 10, 2019

(65) Prior Publication Data

US 2020/0178942 A1 Jun. 11, 2020

(30) Foreign Application Priority Data

Dec. 5, 2018 (TW) ................................ 107143558

(51) Int. Cl.
*A61B 9/00* (2006.01)

(52) U.S. Cl.
CPC .......... *A61B 9/00* (2013.01); *A61B 2560/029* (2013.01); *A61B 2560/0406* (2013.01)

(58) Field of Classification Search
CPC ................ A61B 9/00; A61B 2560/029; A61B 2560/0406; A61B 9/005; A61H 23/02
See application file for complete search history.

(56) References Cited

FOREIGN PATENT DOCUMENTS

| | | | |
|---|---|---|---|
| CN | 204683657 U | * | 10/2015 |
| CN | 108836806 A | * | 11/2018 |

OTHER PUBLICATIONS

Machine translation of CN 108836806 A (Year: 2018).*
Machine translation of CN 204683657-U (Year: 2015).*

* cited by examiner

*Primary Examiner* — David J. McCrosky
(74) *Attorney, Agent, or Firm* — Bacon & Thomas, PLLC

(57) ABSTRACT

The invention relates to an automatic reflection hammer system, which comprises the following components: a reflective hammer chassis, an outer side having a detachable reflection hammer head, and a pulley, a universal joint, a vertical height adjustment mechanism, and a fixing bracket. Wherein, the reflection hammer chassis links with the universal joint, the universal joint links to the vertical height adjustment mechanism, and the vertical height adjustment mechanism links with the fixing bracket.

2 Claims, 4 Drawing Sheets

200

2041
20
204
201
202
203
21
22
23

AUTOMATIC REFLECTION HAMMER SYSTEM

BACKGROUND OF THE INVENTION

1. Field of the Invention

The invention relates to an automatic reflection hammer system, particularly to an automatic reflection hammer system with the functions of angle and direction adjustment, as well as vertical height adjustment function.

2. Description of the Prior Art

When common people (testee) go to the hospital for the neurological examination, as shown in FIG. 1, the neurologist usually uses a small hammer (usually called the reflection hammer or neural hammer) 11, to knock the testee's shank (including knee) 12 for carry on the examination of knee reflex. This kind of examination belongs to the nerval reflection examination.

As the abovementioned description, when the reflection hammer is used to knock the testee's knee, the knee jerk reflex phenomenon will be occurred. The knee jerk reflex (knee jump reflex) is a reflex action. When the knee joint is half crooked and the shank is drooped freely, slightly knocking the lower part of kneecap will cause the contraction of quadriceps femoris muscle, thus, the shank will kick forward. Both the afferent and efferent pathways of reflex are pass through the sumal nerves controlling the quadriceps femoris muscle, and the nerve center lies at the third, fourth coxal sections of spinal cord.

The abovementioned reflex action belongs to the monosynapic reflex, and it only needs the monosynapic pathway to finish the reflex. It does not need the transmission through the interneuron. Slightly knocking the lower part of kneecap will cause the contraction of leg extensor muscle and the stretch of flexor muscle. After the response of muscle, the signal will be transmitted to the spinal cord, and returned to the muscle through the synapse at the anterior horn of spinal cord for finishing the reflex response entirely.

As the abovementioned description, when the knee joint is slightly crooked and the shank is drooped freely, slightly knocking the lower part of kneecap will cause the contraction of quadriceps femoris muscle, and the shank will kick forward. It shows the neural function is normal, and if the knee reflect is weak or disappeared, it may represent that there is the pathological change to the spinal cord or surrounding nerve.

The transmission of general information in the human body is sent to the cerebral cortex through the sensory nerve, which is identified, judged by the cerebrum and then the command is ordered. However, the reflect action does not initiate through the cerebrum. The action is finished directly by the command of medulla oblongata or spinal cord, the response is much faster. Thus the reflect action is one of the protection mechanisms of human body, for example, when the hand touches a very hot pot, if the "scald" feeling is passed to the brain in advance, after been judged by the cerebrum, and the command is ordered to contract back the hand, the hand has already been scalded at this moment. On the contrary, when the information can be transmitted to the spinal cord directly, the motor nerve can be commanded by the spinal cord directly to draw back the hand as soon as possible, in order to avoid scalding.

In the past, the neurological examination should rely on the knock of reflection hammer 11 in FIG. 1 used by the physician. The physician used the manual way to knock the testee's knee. At this moment, it should totally rely on the previous experience of physician and the force applied by the hand to finish the response of knee reflect. Thus, if when the doctor is deficient of knocking experience, or too tired because there are too many patients who are treated every day, there will be uneven state of applied force unavoidably. The knocking force might be too large to make the knee pain of patient, or the force might be unable to be applied while knocking, which makes the knee of patient is unable to produce the reflect response.

As for the occurrence of the abovementioned situation, the neurological sector expects to automatically generate even examination force continuously without any mistake caused by manual operation, under the circumstance that no matter how many patients are treated. Thus, the engineering approach is used to produce the automatic reflection hammer system, which has the greater possibility to substitute the traditional technology. If the automatic reflection hammer system with even force generation can be produced to substitute the traditional reflection hammer, it will be the sincere hope of neurological sector undoubtedly for many years.

SUMMARY OF THE INVENTION

The invention relates to an automatic reflection hammer system, which comprises the following components: a reflective hammer chassis, a universal joint, a vertical height adjustment mechanism, and a fixing bracket. Wherein, the reflection hammer chassis links with the universal joint, the universal joint links to the vertical height adjustment mechanism, and the vertical height adjustment mechanism links with the fixing bracket.

The outer side of the reflective hammer chassis of the invention comprises a detachable reflection hammer head, and a pulley.

The inside of the reflective hammer chassis of the invention comprises a man-machine interface, a circuit control system, and a motor transmission system.

The man-machine interface of the invention has the function of transmitting the control signal to the circuit control system. The circuit control system has the function of controlling the motor transmission system. And the circuit control system has the function of controlling the pulley.

The vertical height adjustment mechanism of the invention has the function of adjusting the vertical height. Thus, the invention uses the vertical height adjustment mechanism to link with the universal joint. When the vertical height adjustment mechanism moves upwards, it can push the reflective hammer chassis upwards. When the vertical height adjustment mechanism moves downwards, it can recover the reflective hammer chassis to the original height.

The reflection hammer chassis of the invention links to the vertical height adjustment mechanism by linking with the universal joint. The detachable reflection hammer head can reach the required knocking angle and direction by adjusting the universal joint.

The circuit control system has the function of controlling the pulley. Therefore, the detachable reflection hammer head can be lifted by the pulley, so that the detachable reflection hammer head becomes the vertical state. After the detachable reflection hammer head is dropped, the "knocking" examination can be finished.

The automatic reflection hammer system of the invention has the function of adjusting the angle and direction. The vertical height adjustment mechanism also has the function of adjusting the vertical height.

The automatic reflection hammer system of the invention can carry on the automatic knocking to reach the function of knee reflex examination.

The invention can continuously produce the even force for examination automatically, there will be no mistake of hand force application, which can totally meet the demand of the medical sector.

In order to further understand the features and technological content of the present invention, please refer to the following detailed description and attached figures of the present invention. Nevertheless, the attached figures are used for reference and description, which are not used for limiting the present invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
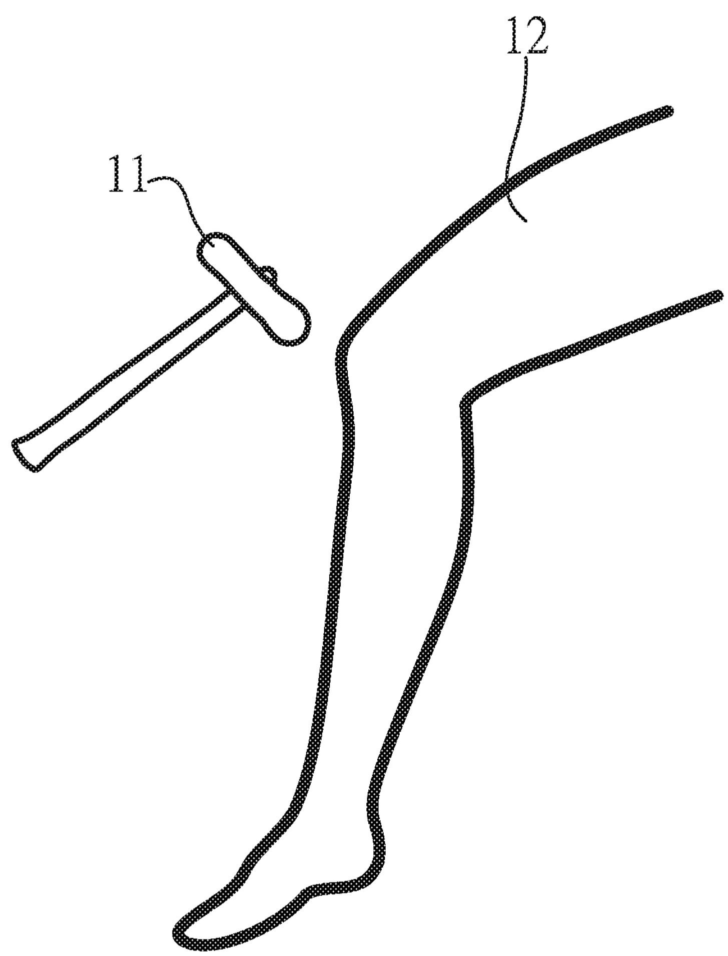
FIG. 1 illustrates the embodiment of conventional reflection hammer.
Figure 2A:
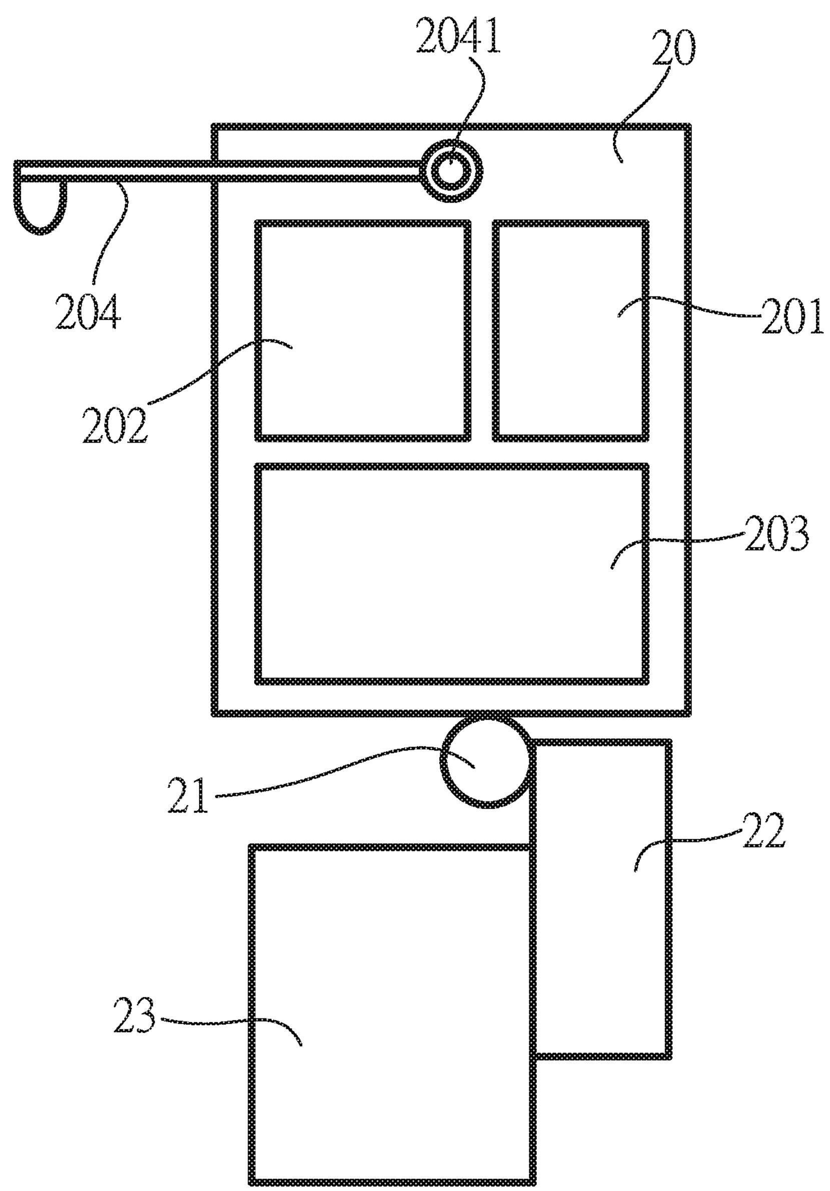
FIG. 2A illustrates the embodiment of the automatic reflection hammer system of the invention.

As shown in FIG. 2A, the embodiment of the automatic reflection hammer system 200 of the invention is illustrated. The automatic reflection hammer system of the invention comprises the following components: a reflective hammer chassis 20 (its outer side having a detachable reflection hammer head 204, and a pulley 2041), a universal joint 21, a vertical height adjustment mechanism 22, and a fixing bracket 23. Wherein, the reflection hammer chassis 20 links with the universal joint 21, the universal joint 21 links to the vertical height adjustment mechanism 22, and the vertical height adjustment mechanism 22 links with the fixing bracket 23.

Still as shown in FIG. 2A, the inside of the reflective hammer chassis 20 comprises: a man-machine interface 201, a circuit control system 202, and a motor transmission system 203. As shown in FIG. 2A, the outer side of the reflective hammer chassis 20 comprises: a detachable reflection hammer head 204, and a pulley 2041. Wherein, the detachable reflection hammer head 204 is installed at the outer side of the reflective hammer chassis 20 by the pulley 2041.

As shown in FIG. 2A, the man-machine interface 201 has the function of transmitting the control signal to the circuit control system 202. The circuit control system 202 has the function of controlling the motor transmission system 203. And the circuit control system 202 has the function of controlling the pulley 2041. The motor transmission system 203 has the function of providing the transmission power. Wherein, the man-machine interface 201 is encapsulated in the reflective hammer chassis 20, the circuit control system 202 and the motor transmission system 203 are located inside the reflective hammer chassis 20.

Figure 2B:
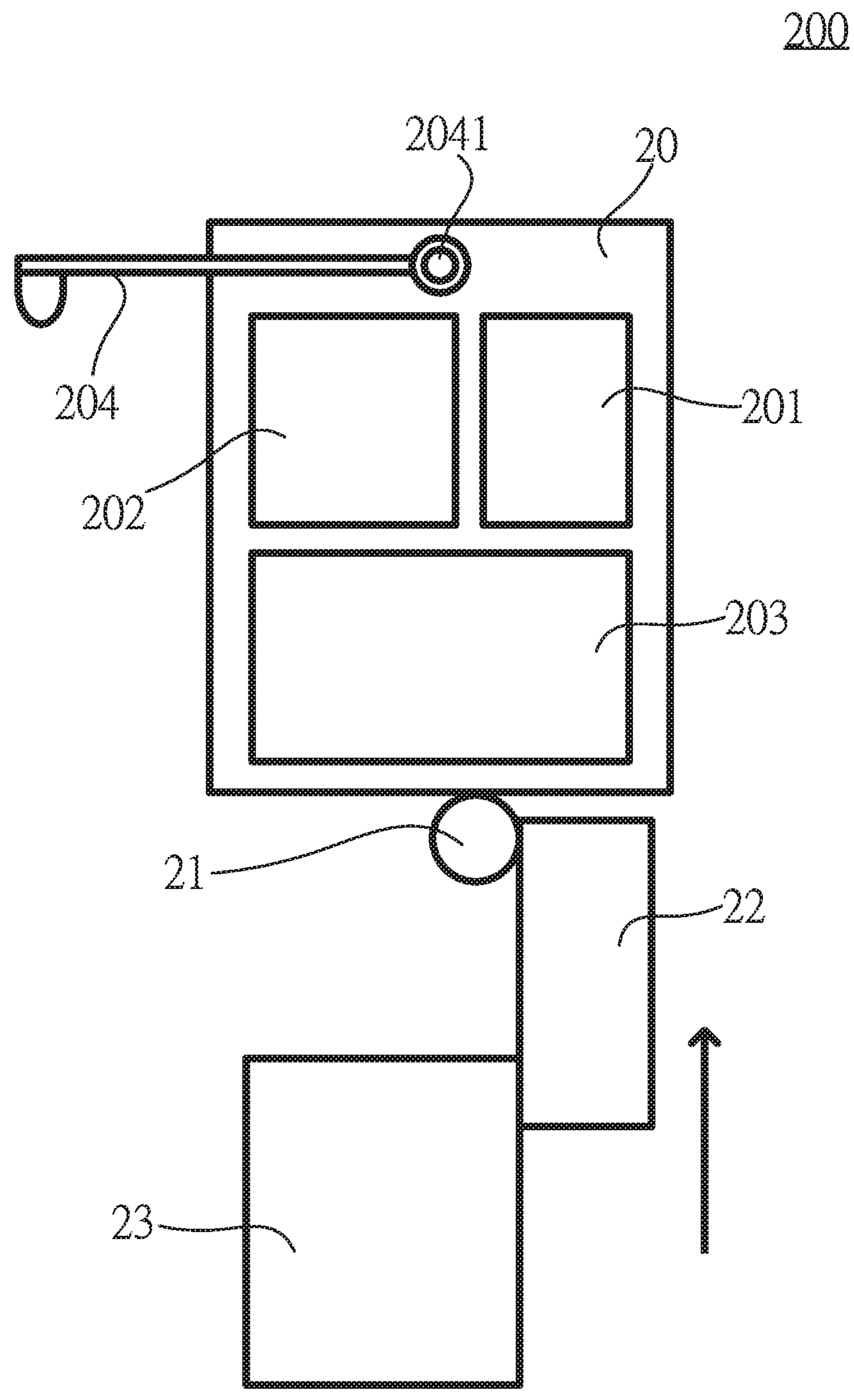
FIG. 2B illustrates the embodiment for the height adjustment of the automatic reflection hammer system of the invention.

As shown in FIG. 2B, the embodiment for the height adjustment of the automatic reflection hammer system of the invention is illustrated. The vertical height adjustment mechanism 22 has the function of adjusting the vertical height. Thus the invention uses the vertical height adjustment mechanism 22 to link with the universal joint 21. When the vertical height adjustment mechanism 22 moves upwards, it can push the reflective hammer chassis 20 upwards. When the vertical height adjustment mechanism 22 moves downwards (recovered to the height shown in FIG. 2A), it can recover the reflective hammer chassis 20 to the original height. Briefly speaking, it can be confirmed that the vertical height adjustment mechanism 22 has the function of adjusting the vertical height of the automatic reflection hammer system 200.

As shown in FIG. 2B, the universal joint 21 has the function of adjusting the angle and direction. Wherein, the reflection hammer chassis 20 links to the vertical height adjustment mechanism 22 by linking with the universal joint 21. The detachable reflection hammer head 204 can reach the required knocking angle and direction by adjusting the universal joint 21 (because the detachable reflection hammer head 204 is installed at the outer side of the reflective hammer chassis 20).

Figure 2C:
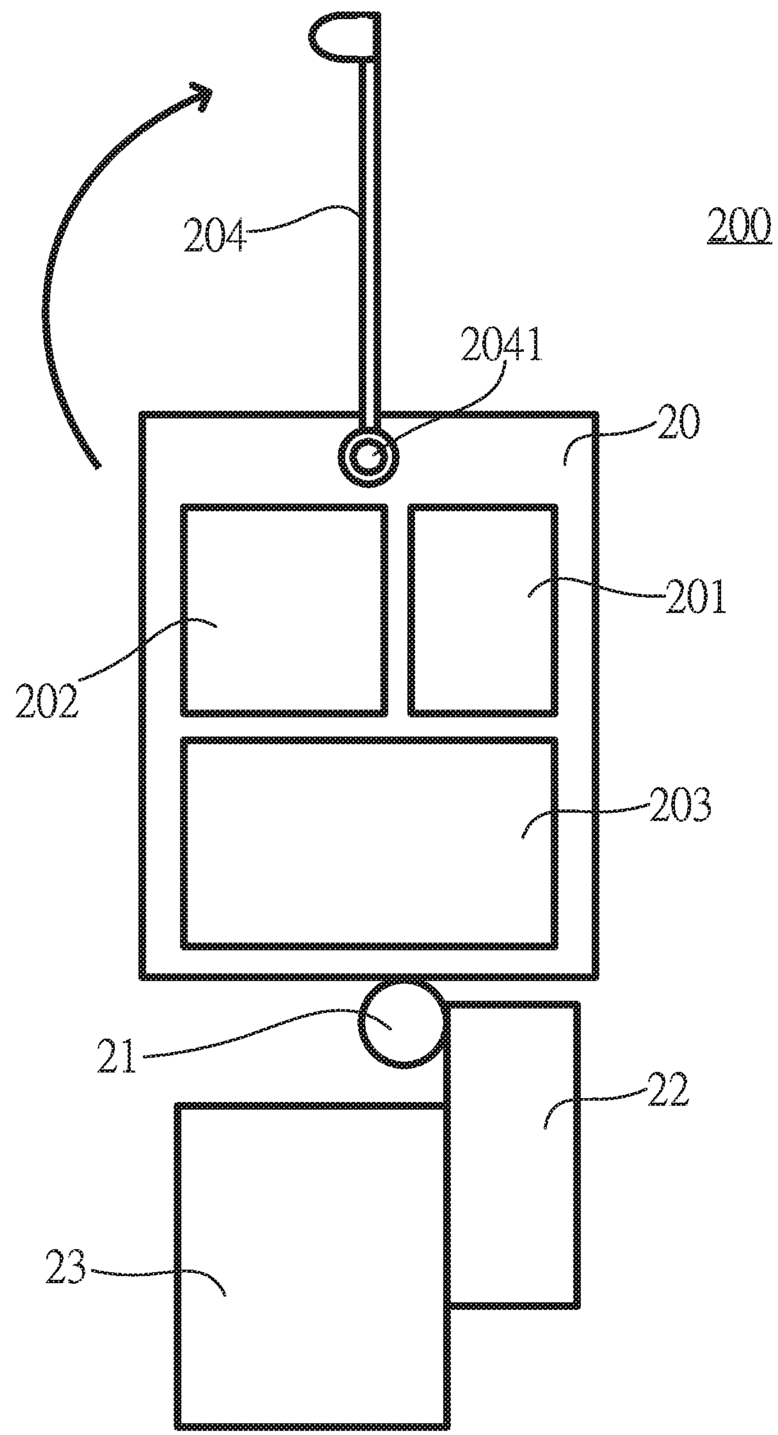
FIG. 2C illustrates the embodiment for the lifting of the automatic reflection hammer system of the invention.

As shown in FIG. 2C, the embodiment for the lifting of the automatic reflection hammer system of the invention is illustrated. When the knocking examination is required, because the circuit control system 202 has the function of controlling the pulley 2041, thus, the detachable reflection hammer head 204 can be lifted by the pulley 2041, so that the detachable reflection hammer head 204 becomes the vertical state. After the detachable reflection hammer head 204 is dropped (recovered to the flat position of the detachable reflection hammer head 204 shown in FIG. 2A), the "knocking" examination can be finished.

Still as shown in FIG. 2C, the fixing bracket 23 has the function of providing the support and stability. The vertical height adjustment mechanism 22 can link to the fixing bracket 23 for maintaining the fixing and stability of the automatic reflection hammer system 200.

Therefore, in the automatic reflection hammer system 200 of the invention, the universal joint 21 has the function of adjusting the angle and direction, the vertical height adjustment mechanism 22 has the function of adjusting the vertical height, and the detachable reflection hammer head 204 has the function of reaching the "knocking" examination.

The automatic reflection hammer system 200 of the invention can carry on the automatic knocking to reach the function of knee reflex examination. And the invention can continuously produce the even force for examination automatically, there will be no mistake of hand force application, which can totally meet the demand of the medical sector.

It is understood that various other modifications will be apparent to and can be readily made by those skilled in the art without departing from the scope and spirit of the invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which the invention pertains.

What is claimed is:

1. An automatic reflection hammer system, comprising:

a reflective hammer chassis, comprising:

a motor transmission apparatus, wherein said motor transmission apparatus has a function of providing a transmission power;

a circuit control apparatus, wherein said circuit control apparatus has a function of controlling said motor transmission apparatus, and said circuit control apparatus has a function of controlling a pulley; and a man-machine interface, wherein said man-machine interface has a function of transmitting a control signal to said circuit control apparatus;

an outer side of said reflective hammer chassis, comprising:

a detachable reflection hammer head; and said pulley, wherein said pulley lifts said detachable reflection hammer head, so that said detachable reflection hammer head is in a vertical state, in order to drop said detachable reflection hammer head;

a universal joint;

a vertical height adjustment mechanism apparatus, wherein when said vertical height adjustment mechanism apparatus moves upwards, said reflective hammer chassis is pushed upwards, and when said vertical height adjustment mechanism apparatus moves downwards, said reflective hammer chassis recovers to an original height; and a fixing bracket, wherein, the reflective hammer chassis links with the universal joint, the universal joint links to the vertical height adjustment mechanism apparatus, and the vertical height adjustment mechanism apparatus links with the fixing bracket.

2. An automatic reflection hammer system having a motor transmission apparatus and a universal joint, comprising:

a reflective hammer chassis, comprising:

a motor transmission apparatus, wherein said motor transmission apparatus has a function of providing a transmission power;

a circuit control system, wherein said circuit control apparatus has a function of controlling said motor transmission apparatus, and said circuit control apparatus has a function of controlling said pulley; and a man-machine interface, wherein said man-machine interface has a function of transmitting a control signal to said circuit control apparatus;

an outer side of said reflective hammer chassis, comprising:

a detachable reflection hammer head; and said pulley, wherein said pulley lifts said detachable reflection hammer head, so that said detachable reflection hammer head is in a vertical state, in order to drop said detachable reflection hammer head;

a universal joint, the universal joint having a function of adjusting an angle and direction;

a vertical height adjustment mechanism apparatus, the vertical height adjustment mechanism apparatus having a function of adjusting a vertical height, wherein when the vertical height adjustment mechanism apparatus moves upwards, the reflective hammer chassis is pushed upwards, and when the vertical height adjustment mechanism apparatus moving downwards, the reflective hammer chassis recovers to an original height; and a fixing bracket, the fixing bracket having a function of providing a support and stability, the reflective hammer chassis linking with the universal joint, the universal joint linking to the vertical height adjustment mechanism apparatus, and the vertical height adjustment mechanism apparatus linking to the fixing bracket.

* * * * *